(12) United States Patent
Hebrank

(10) Patent No.: US 7,333,187 B2
(45) Date of Patent: Feb. 19, 2008

(54) METHODS AND APPARATUS FOR IDENTIFYING AND DIAGNOSING LIVE EGGS USING HEART RATE AND EMBRYO MOTION

(75) Inventor: John H. Hebrank, Durham, NC (US)

(73) Assignee: Embrex, Inc., Durham, NC (US)

( * ) Notice: Subject to any disclaimer, the term of this patent is extended or adjusted under 35 U.S.C. 154(b) by 146 days.

(21) Appl. No.: 11/218,013

(22) Filed: Sep. 1, 2005

(65) Prior Publication Data
US 2006/0082759 A1   Apr. 20, 2006

Related U.S. Application Data

(60) Provisional application No. 60/674,742, filed on Apr. 26, 2005, provisional application No. 60/618,812, filed on Oct. 14, 2004.

(51) Int. Cl.
*A01K 43/00* (2006.01)
*A01K 43/04* (2006.01)
*A01K 45/00* (2006.01)
*G01N 33/08* (2006.01)

(52) U.S. Cl. .............................. 356/53; 356/52; 356/54; 119/6.8; 209/510; 209/511

(58) Field of Classification Search ...................... None
See application file for complete search history.

(56) References Cited

U.S. PATENT DOCUMENTS 3,540,824 A    11/1970  Fonda et al.

| 4,458,630 A | | 7/1984 | Sharma et al. |
| 4,604,968 A | * | 8/1986 | Christensen ................. 119/6.8 |
| 4,671,652 A | | 6/1987 | van Asselt et al. |
| 4,681,063 A | | 7/1987 | Hebrank |

(Continued)

FOREIGN PATENT DOCUMENTS

JP           9127096 A2     5/1997

(Continued)

OTHER PUBLICATIONS

International Search Report and Written Opinion for International Application No. PCT/US2005/34626; Mailed Feb. 13, 2007.

*Primary Examiner*—Gregory J. Toatley, Jr.
*Assistant Examiner*—Gordon J. Stock, Jr.
(74) *Attorney, Agent, or Firm*—Myers Bigel Sibley & Sajovec, P.A.

(57) ABSTRACT

Identifying live eggs includes: a) illuminating eggs with light; b) receiving light passing through each egg at a light detector; c) generating an output signal that corresponds to light received at a light detector for each respective egg; d) analyzing the output signals to identify an indication of an external disturbance; e) analyzing the output signal for each egg to identify the existence of an embryo heart rate and/or embryo movement; and f) designating an egg as a live egg in response to identifying embryo heart rate and/or embryo movement. Steps a) through d) are repeated if output signals from a predetermined number of eggs contain an indication of an external disturbance to the eggs. Steps a) through f) are repeated if the number of eggs designated as live exceeds an expected number, or if embryo movement occurs at about the same time in a predetermined number of eggs.

37 Claims, 5 Drawing Sheets

U.S. PATENT DOCUMENTS

| | | |
|---|---|---|
| 4,914,672 A | 4/1990 | Hebrank |
| 4,955,728 A | 9/1990 | Hebrank |
| 5,017,003 A | 5/1991 | Keromnes et al. |
| 5,028,421 A | 7/1991 | Fredericksen et al. |
| 5,158,038 A | 10/1992 | Sheeks et al. |
| 5,173,737 A | 12/1992 | Mitchell et al. |
| 5,745,228 A | 4/1998 | Hebrank et al. |
| 6,145,668 A | 11/2000 | DePauw et al. |
| 6,149,375 A | 11/2000 | Hebrank |
| 6,213,709 B1 | 4/2001 | Hebrank |
| 6,224,316 B1 | 5/2001 | Hebrank et al. |
| 6,427,844 B2 * | 8/2002 | Hebrank .................. 209/510 |
| 6,488,156 B1 | 12/2002 | Cohen |
| 6,750,954 B2 | 6/2004 | Hebrank et al. |
| 6,860,225 B2 | 3/2005 | Hebrank |
| 2002/0014444 A1 * | 2/2002 | Hebrank .................. 209/510 |
| 2003/0227613 A1 | 12/2003 | Hebrank |
| 2004/0065263 A1 | 4/2004 | Hebrank et al. |

FOREIGN PATENT DOCUMENTS

| | | |
|---|---|---|
| SU | 1226308 A | 4/1986 |
| WO | WO 02/086495 | 10/2002 |
| WO | WO 2004/023136 | 3/2004 |
| WO | WO 2004023136 A2 * | 3/2004 |

* cited by examiner

US 7,333,187 B2

METHODS AND APPARATUS FOR IDENTIFYING AND DIAGNOSING LIVE EGGS USING HEART RATE AND EMBRYO MOTION

RELATED APPLICATIONS

This application claims the benefit of and priority to U.S. Provisional Patent Application No. 60/618,812, filed Oct. 14, 2004, and U.S. Provisional Patent Application No. 60/674,742, filed Apr. 26, 2005, the disclosures of which are incorporated herein by reference as if set forth in their entirety.

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent and, when placed in front of direct light, the contents of an egg can be observed.

Eggs which are to be hatched to live poultry are typically candled during embryonic development to identify clear, rotted, and dead eggs (collectively referred to herein as "non-live eggs"). Non-live eggs are typically removed from incubation to increase available incubator space. In many instances it is desirable to introduce a substance, via in ovo injection, into a live egg prior to hatch. Injections of various substances into avian eggs are typically employed in the commercial poultry industry to decrease post-hatch mortality rates or increase the growth rates of the hatched bird. Examples of substances that have been used for, or proposed for, in ovo injection include vaccines, antibiotics and vitamins. Examples of in ovo treatment substances and methods of in ovo injection are described in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. An example of an in ovo injection device is disclosed in U.S. Pat. No. 4,681,063 to Hebrank. This device positions an egg and an injection needle in a fixed relationship to each other, and is designed for high-speed automated injection of a plurality of eggs. The selection of both the site and time of injection treatment can impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for identifying live eggs and selectively injecting only live eggs, is desirable.

In commercial turkey production, a significant number of valuable eggs die during the hatching process. These deaths could be prevented by various intervention techniques such as cracking the air cell to aid pipping, placing the egg in a more oxygen rich environment, placing the egg in a warmer environment, and/or administering treatment (e.g., a thyroid releasing hormone). Unfortunately, it can be difficult to detect eggs that require intervention.

There are other applications where it is important to be able to identify live and non-live eggs. One of these applications is the cultivation and harvesting of vaccines in live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo, and then harvesting the amniotic fluid from the egg. Typically, eggs are candled before injection of a seed virus to facilitate removal of non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 4,671,652 to van Asselt et al. describes a candling apparatus in which a plurality of light sources and corresponding light detectors are mounted in an array, and wherein eggs are passed on a flat between the light sources and the light detectors.

Japanese Patent No. JP9127096A2 describes an apparatus that detects pulse rate of egg embryos in order to identify live and dead eggs. PCT Publication WO 02/086495 describes an apparatus for determining the viability of an egg by detecting heart rate. USSR Patent Application No. SU1226308A1 describes scanning egg embryos for the presence of blood vessels in order to determine viability. U.S. Pat. No. 3,540,824 describes a method and apparatus for detecting heart beats in incubating egg embryos. U.S. Pat. No. 6,488,156 describes the use of electrical sensors placed on the shell of an egg for the purpose of measuring heart rate.

As in humans, the heart rate of a bird, such as a chicken, can indicate the condition or health of the bird. In the extreme, absence of a heart rate can indicate death. With respect to humans, a heart rate in the range of 60 to 180 beats per minute can indicate metabolic load (i.e., the amount of oxygen that needs to be transported through the body), health, and/or the condition of the heart itself. The heart rate of a Day 18 chicken embryo is typically between about 200 and 300 beats per minute in an incubator at 37° C. Removing the egg from the incubator and into an area with a lower temperature, such as a room at 25° C., produces a characteristic heart rate pattern. First, heart rate accelerates by about 20%, presumably as the animal is awakened or startled by the motion, light, or perhaps even sound or vibration. After two or three minutes, the embryo heart rate settles back down and then slowly declines to about 50% of the baseline heart rate over forty-five minutes as the egg slowly cools, as illustrated in FIG. 1. Thus, although embryo heart rate can be used to indicate the health or condition of the embryo, its accuracy can be affected because of the effect external stimuli and environmental conditions surrounding an egg can have on the embryo.

In addition to heart rate detection methods, the detection of embryo motion can be indicative of a live egg. Detection of embryo motion and embryo heart rate can be performed by monitoring changes in light levels within an egg when the egg is illuminated with light from a candling apparatus. Embryo motion produces relatively large signals so that there are few false lives (i.e., non-live embryos indicated as live) created by external disturbances, vibrations, etc. imparted to an egg carrier. However, not every live embryo will move in a given time interval, so false deads (i.e., live embryos indicated as dead) can be common for candling intervals of ten seconds and less. Detection of an embryo heart rate may require, for example, about a hundred-fold increase in sensitivity as compared with embryo motion detection. However, an embryo heart rate provides a continuously available signal.

To reduce the number of false lives as a result of external disturbances, heart rate detection candling systems are generally configured to detect multiple cycles of an embryo heart rate. Unfortunately, longer candling times generally decrease egg throughput and typically require more candling detectors in order to compensate for the longer candling times. Heart rate detection methods that allow faster detection times with fewer false lives caused by external vibrations are desirable.

SUMMARY OF THE INVENTION

In view of the above discussion, a method of identifying live eggs, according to embodiments of the present invention, includes a) illuminating eggs in a carrier with light from a light source; b) receiving light passing through each egg at a light detector; c) generating an output signal that corresponds to light received at a light detector for each respective egg; d) analyzing the output signals for the eggs to identify an indication (e.g., noise, waveforms, etc.) of an external disturbance imparted to the carrier; e) analyzing the output signal for each egg to identify the existence of an embryo heart rate and/or embryo movement; and f) designating an egg as a live egg in response to identifying embryo heart rate and/or embryo movement. In response to determining that output signals from a predetermined number of eggs contain an indication of an external disturbance imparted to the carrier, steps a) through d) are repeated. Also, the number of eggs designated as live can be compared with an expected number and, in response to determining that the number of eggs designated as live exceeds the expected number, steps a) through f) are repeated. Also, the time at which embryo movement is identified is recorded and in response to determining that embryo movement occurred at about the same time in a predetermined number of eggs, steps a) through f) are repeated.

According to embodiments of the present invention, a candling apparatus that identifies live eggs among a plurality of eggs within a carrier, includes a light source that illuminates one or more eggs within the carrier with light; a detector that receives light passing through one or more eggs from the light source and that generates an output signal corresponding to the received light; and a processor configured to analyze the output signal for each egg for the existence of embryo heart rate and/or embryo movement. The processor is configured to designate an egg as a live egg in response to identifying embryo heart rate and/or embryo movement, and the processor is configured to analyze the output signal for each egg to identify an indication (e.g., noise, waveforms, etc.) of an external disturbance imparted to the carrier. The processor is configured to require that the plurality of eggs be recandled in response to determining that output signals from a predetermined number of eggs contain an indication of an external disturbance. In addition, the processor is configured to compare the number of eggs designated as live with an expected number, and to require that the plurality of eggs be recandled in response to determining that the number of eggs designated as live exceeds an expected number. The processor is configured to record the time at which embryo motion is identified for each egg, and to require that the plurality of eggs be recandled in response to determining that embryo movement occurred at about the same time in a predetermined number of eggs.

According to embodiments of the present invention, embryo heart rate and/or movement can be used as a diagnostic tool for live eggs. For example, embryo heart rates of each of a plurality of embryonated eggs are measured and an average embryo heart rate for the plurality of eggs is determined. A respective embryo heart rate for each egg is compared with the average embryo heart rate to identify eggs having embryos with heart rates that deviate from the average heart rate. A deviating heart rate (i.e., a higher heart rate than average or a lower heart rate than average) may indicate a negative health condition of an embryo, for example. In response to identifying an egg having a deviating heart rate, some function designed to improve the negative health condition of the egg can be performed such as, for example, cracking the egg air cell to aid pipping, placing the egg in an oxygen-enhanced environment, placing the egg in a warmer environment, and injecting material (e.g., vaccines, medications, nutrients, hormones, etc.) into the egg. Eggs with similar heart rates may be grouped for special incubation conditions or further treatment.

According to embodiments of the present invention, embryo motion is measured for each of a plurality of eggs in a carrier and then an average embryo motion for the plurality of eggs is determined. A respective embryo motion for each egg is compared with the average embryo motion to identify eggs having embryos with motion that deviates from the average motion. A deviating amount of motion (i.e., less motion than average or higher motion than average) may indicate a negative health condition of an embryo, for example. In response to identifying an egg having a deviating amount of embryo motion, some function designed to improve the negative health condition of the egg can be performed such as, for example, cracking the egg air cell to aid pipping, placing the egg in an oxygen-enhanced environment, placing the egg in a warmer environment, and injecting material (e.g., vaccines, medications, nutrients, hormones, etc.) into the egg.

According to other embodiments of the present invention, identifying the gender of a plurality of eggs may be performed by measuring heart rates of each of a plurality of eggs; determining an average heart rate for the plurality of eggs; and comparing the respective heart rate for each egg with the average heart rate to identify a gender of each egg or a subset of the eggs with extreme heart rates.

According to other embodiments of the present invention, diagnosing embryo health of a plurality of eggs includes measuring embryo motion of each of a plurality of eggs; determining average embryo motion for the plurality of eggs; and comparing the respective embryo motion for each egg with the average embryo motion to identify eggs having embryo motion that deviates from the average embryo motion.

According to other embodiments of the present invention, diagnosing embryo health of a plurality of eggs includes measuring heart rates of each of a plurality of eggs; measuring temperature of each of the plurality of eggs; determining an average heart rate and average temperature for the plurality of eggs; and comparing the respective heart rate and temperature for each egg with the average heart rate and temperature to identify eggs having embryos with heart rates and temperatures that deviate from the average heart rate and average temperature.

According to other embodiments of the present invention, diagnosing embryo health of a plurality of eggs includes measuring heart rates of each of a plurality of eggs; measuring egg shell size of each of the plurality of eggs; determining an average heart rate and egg shell size for the plurality of eggs; and comparing the respective heart rate and egg shell size for each egg with the average heart rate and egg shell size to identify eggs having embryos with heart rates and egg shell sizes that deviate from the average heart rate and average egg shell size.

According to other embodiments of the present invention, diagnosing embryo health of a plurality of eggs includes measuring heart rates of each of a plurality of eggs; measuring egg weight of each of the plurality of eggs; determining an average heart rate and egg weight for the plurality of eggs; and comparing the respective heart rate and egg weight for each egg with the average heart rate and egg weight to identify eggs having embryos with heart rates and egg weights that deviate from the average heart rate and average egg weight.

DETAILED DESCRIPTION OF THE INVENTION

Figure 1:
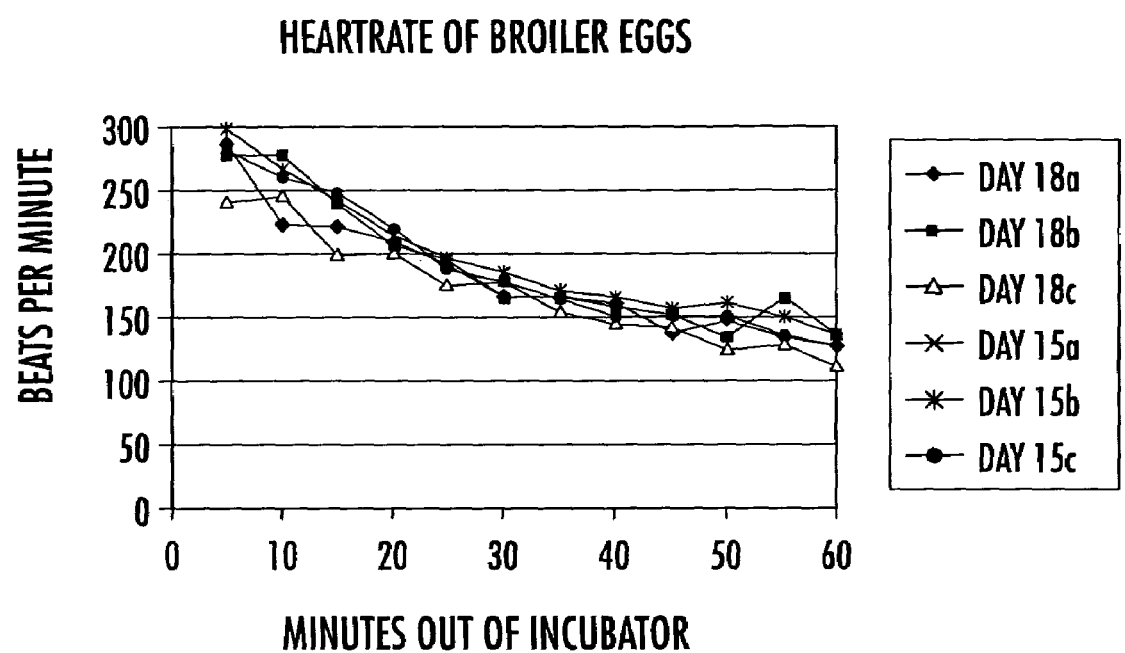
FIG. 1 illustrates how a change of environment affects the heart rate of a chicken embryo.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

The detection of avian embryo heart rate and/or motion, according to embodiments of the present invention, may occur at any time during embryonic development (also referred to as the incubation period). Embodiments of the present invention are not limited to heart rate and/or motion detection only at a particular day (e.g., Day-11) or time period during the embryonic development period. In addition, methods and apparatus according to embodiments of the present invention may be used with any types of avian eggs including, but not limited to, chicken, turkey, duck, geese, quail, pheasant eggs, exotic bird eggs, etc.

In environments, such as commercial hatcheries, where in-ovo embryo motion and/or heart rate are measured, multiple eggs are conventionally processed at the same time. For example, multiple eggs within an egg flat are conventionally candled for embryo motion and/or embryo heart rate at the same time. Various methods of measuring embryo heart rates and/or embryo motion may be used in accordance with embodiments of the present invention. For example, each egg may be illuminated with light from a light source (e.g., either or both visible and infrared wavelengths). Light leaving each egg is then received by a photodetector typically positioned adjacent to each egg. Each photodetector generates an output signal that corresponds to the intensity of light leaving a respective egg. The output signal is processed to determine the embryo heart rate of each respective egg. For example, an output signal may be processed to determine the existence of cyclical variations in light intensity that correspond to an embryo heart rate. In addition, an output signal may be processed to determine the existence of non-cyclical variations in light intensity that correspond to embryo movement within an egg.

Figure 2:
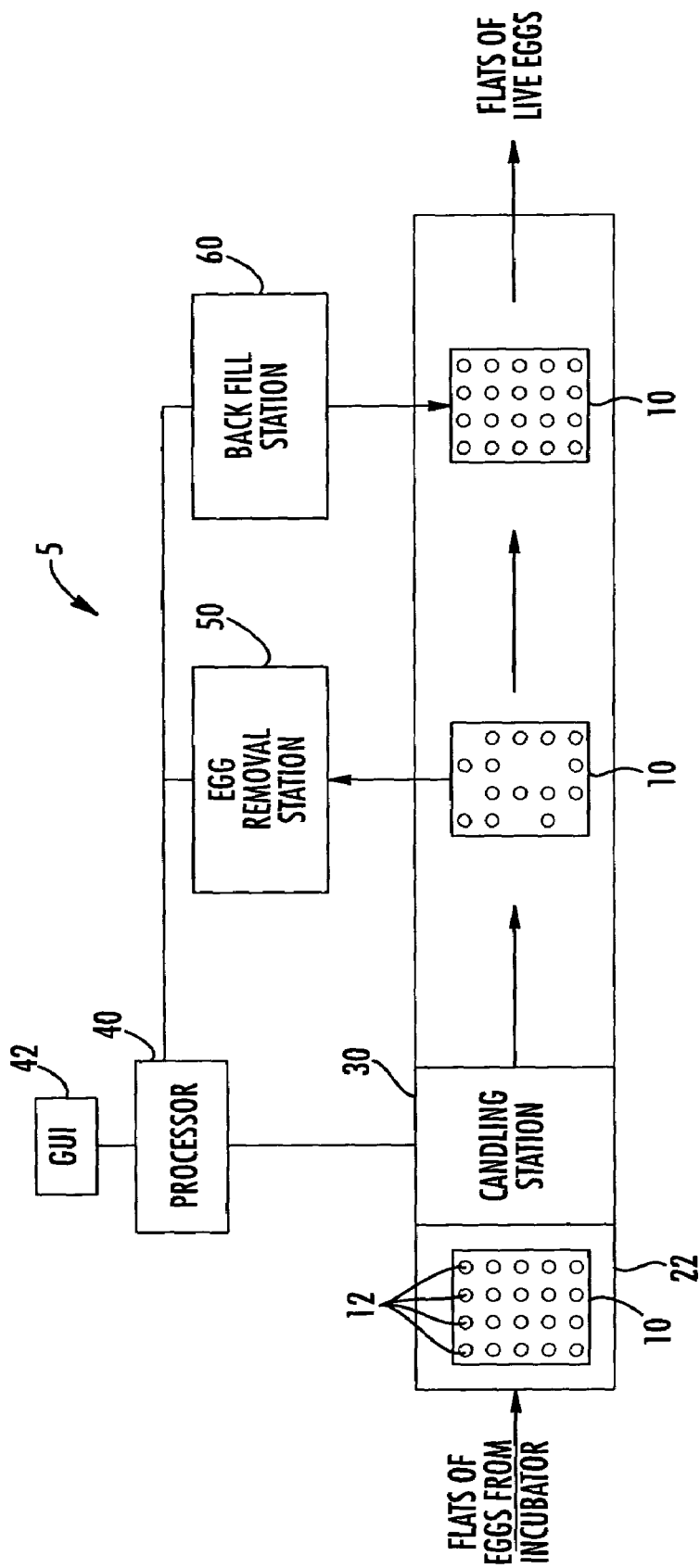
FIG. 2 is a block diagram of an apparatus that identifies live eggs, according to embodiments of the present invention.

FIG. 2 is a block diagram of an apparatus 5 that identifies live eggs, according to embodiments of the present invention. A carrier (e.g., an egg flat) 10 of eggs 12 is conveyed via a conveyor 22 to a candling station 30 that is configured to designate each egg 12 within the flat 10 as being either live or non-live based on the detection of, or absence of, embryo heart rate and/or movement. Any type of conveying system suitable for conveying flats of eggs may be utilized in accordance with embodiments of the present invention. Egg conveying systems are well known to those of skill in the art and need not be described further herein.

Although eggs conventionally are carried in egg flats, any means of presenting a plurality of eggs over time to a candling station 30, as well as to other egg processing equipment, may be used. Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

The candling station 30 includes a light source that illuminates each egg within a carrier with light and a detector that receives light passing through each egg from the light source and that generates an output signal that corresponds to received light. An exemplary light candling system that may be utilized in accordance with embodiments of the present invention is described in U.S. Pat. No. 5,745,228 to Hebrank et al. A suitable commercial light candling system includes the S Beam light candling system of the Vaccine Saver™ vaccine delivery system available from Embrex, Inc. of Research Triangle Park, N.C. The candling station 30 may also include an optical system that illuminates each egg and measures the light coming from each egg as described in U.S. Pat. No. 6,860,225 to Hebrank.

The candling station 30 in the illustrated embodiment is operatively connected to a processor 40 which controls operations of the candling station 30, analyzes the output signal from each detector and stores information received from the candling station 30 about each egg 12. An operator interface (e.g., a graphical user interface (GUI), or other type of display) 42 may be provided to allow an operator to interact with the processor 40. The processor 40 may control various other downstream egg processing operations, as well, including an egg removal station 50 and backfill station 60.

The processor 40 analyzes the output signal for each egg to identify the existence of an embryo pulse and/or embryo movement and then designates an egg as a live or non-live egg in response thereto. According to embodiments of the present invention, the processor 40 analyzes the output signal for each egg to identify an indication of an external disturbance imparted to an egg flat 10. For example, the processor 40 analyzes the output signal for noise and/or for one or more waveforms that are indication of an external disturbance. If output signals from more than or equal to a predetermined number of eggs contain an indication of an external disturbance, the processor 40 instructs the candling station to re-candle the eggs 12. The processor 40 also compares the number of eggs designated as live with an expected number and directs the candling station 30 to re-candle the eggs 12 in the flat 10 in response to determining that the number of eggs designated as live exceeds the expected number. The processor 40 also directs the candling station 30 to re-candle the eggs 12 if embryo movement is detected in multiple eggs at the same time.

According to embodiments of the present invention, the processor 40 is configured to statistically correlate times that a particular waveform portion is detected for each egg and to use this to predict the likelihood that a single external event affected some or all of the eggs in a flat. For example, the processor 40 can be configured to record the time at which a particular output signal (e.g., waveform maximum, waveform zero crossing, etc.) occurred for each egg. The processor 40 also directs the candling station 30 to re-candle the eggs 12 in response to determining that a particular output signal occurred at about the same time in a predetermined number of eggs. As would be understood by one skilled in the art, the term "waveform zero crossing" means where a waveform crosses the "X" axis (i.e., a "Y" value of zero). Thus, for example, if a majority of eggs in a flat have a waveform peak that occurs at the same time, the processor 40 will direct the candling station to re-candle the eggs.

Eggs 12 designated as non-live are removed from the flat 10 downstream from the candling station 30 at egg removal station 50. According to embodiments of the present invention, the processor 40 generates a selective removal signal for eggs determined to be non-live. The non-live eggs are removed from the flat 10 and discarded or used for some other purpose.

The egg removal station 50 may be a manual station wherein the designated non-live eggs are removed by hand or marked for later removal. Alternatively, the egg removal station 50 may operate automatically and robotically. For example, the egg removal station 50 may employ suction-type lifting devices as disclosed in U.S. Pat. No. 4,681,063 or in U.S. Pat. No. 5,017,003 to Keromnes et al. Various devices and methods for automatically and robotically removing eggs from a flat and transporting same to another location may be utilized with embodiments of the present invention without limitation. Exemplary egg removal apparatus that may serve the function of the egg removal station 50 are described in U.S. Pat. Nos. 6,145,668; 6,149,375; 6,213,709; and 6,224,316. Alternatively, live eggs may be removed from the flat 10 and non-live eggs may be left in the flat 10.

In the illustrated embodiment, the vacancies in the flat 10 created by removing non-live eggs are filled with live eggs from another source via backfill station 60. The backfill station 60 may be a manual station wherein eggs are manually moved or may be an automated station that moves eggs automatically and robotically.

Flat 10 at this point on the conveyor 22 contains only live eggs 12 and can proceed to processing (e.g., inoculation, vaccine production, etc.). An exemplary device for in ovo injection of substances into a plurality of eggs in accordance with embodiments of the present invention is the INOVOJECT® automated injection system (Embrex, Inc., Research Triangle Park, N.C.). However, any in ovo injection device may be suitable for use according to embodiments of the present invention. Suitable injection devices preferably are designed to operate in conjunction with commercial egg carrier devices or flats.

According to other embodiments of the present invention described herein, the processor 40 utilizes embryo heart rate as a diagnostic tool. For example, the processor 40 is configured to measure embryo heart rates of each of a plurality of presumably embryonated eggs and determine an average embryo heart rate for the plurality of eggs. The processor 40 compares the respective embryo heart rate for each egg with the average embryo heart rate to identify eggs having embryos with heart rates that deviate from the average heart rate. A deviating heart rate (i.e., a higher heart rate than average or a lower heart rate than average) may indicate a negative health condition of an embryo, for example. The processor 40 may also be configured to measure embryo motion for a plurality of eggs, and calculate an average motion for the plurality of eggs. The processor 40 then compares respective embryo motion for each egg with the average embryo motion to identify eggs having embryos with motion that deviates from the average motion. A deviating amount of motion (i.e., less motion than average or higher motion than average) may indicate a negative health condition of an embryo, for example.

Disturbances to an egg carrier from external sources (e.g., environmental vibrations, machine vibrations, physical impact, etc.) will affect most or all eggs in the carrier at about the same time. For example, if an egg flat experiences a physical disturbance (e.g., a jolt, external vibration, an operator inadvertently bumping the egg flat, etc.), the eggs in the flat will all experience the physical disturbance and a light signal coming from each egg during candling likely will contain an indication (e.g., noise and/or one or more waveforms) of the occurrence of the physical disturbance. According to embodiments of the present invention, by detecting noise/waveforms in the light signal from multiple eggs, it can be determined that an external disturbance occurred that gave the appearance of embryo movement and that the eggs should be recandled to avoid false live indications.

Figure 3:
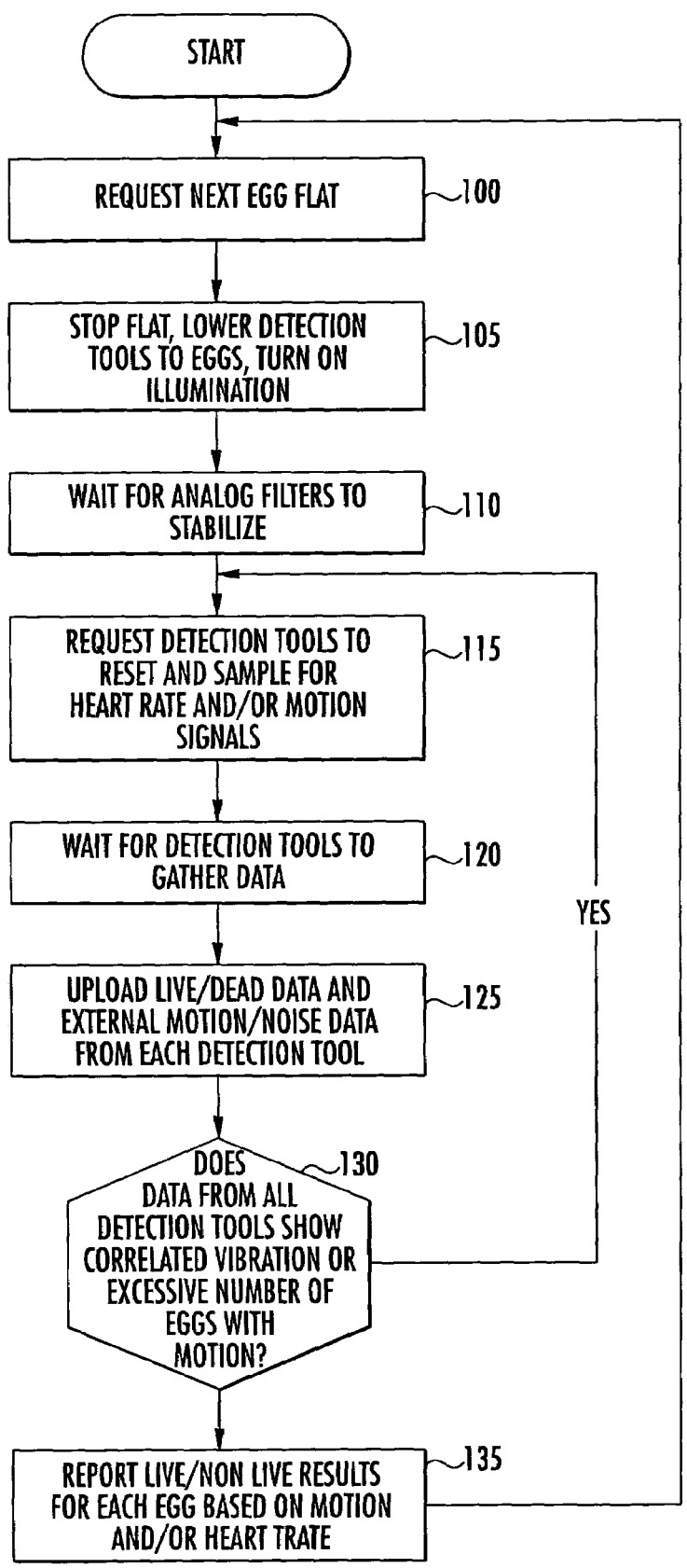
FIGS. 3-4 are flow charts of operations for identifying live eggs, according to embodiments of the present invention.

Referring to FIG. 3, operations for identifying live and non-live eggs, according to embodiments of the present invention, wherein external disturbances are identified and accounted for, are illustrated. An egg flat is requested and conveyed to a candling station (e.g., candling station 30 of FIG. 2) (Block 100). When the egg flat is in position, the detection tools (i.e., light source and/or detector) are lowered (or raised) such that one or more eggs in the flat can be candled for embryo heart rate and/or embryo movement (Block 105). The analog filters associated with the detection tools are allowed to stabilize (Block 110), as would be understood by one skilled in the art, and then the detection tools sample for embryo heart rate and/or embryo movement (Block 115). The detection tools gather data for each egg (Block 120) and then upload this data to storage (Block 125). A processor (e.g., processor 40 of FIG. 2) analyzes the data for correlated vibration and/or excessive numbers of eggs exhibiting embryo movement (Block 130). As described below with respect to FIG. 4, an external disturbance to an egg flat can cause the eggs in the flat to simulate embryo movement when, in fact, there has been no embryo movement at all. If it is suspected that an external disturbance has been imparted to the egg flat, recandling of the eggs is requested (Block 115). Results as to whether an egg is live or non-live based on detected heart rate and/or motion is then reported (Block 135).

Figure 4:
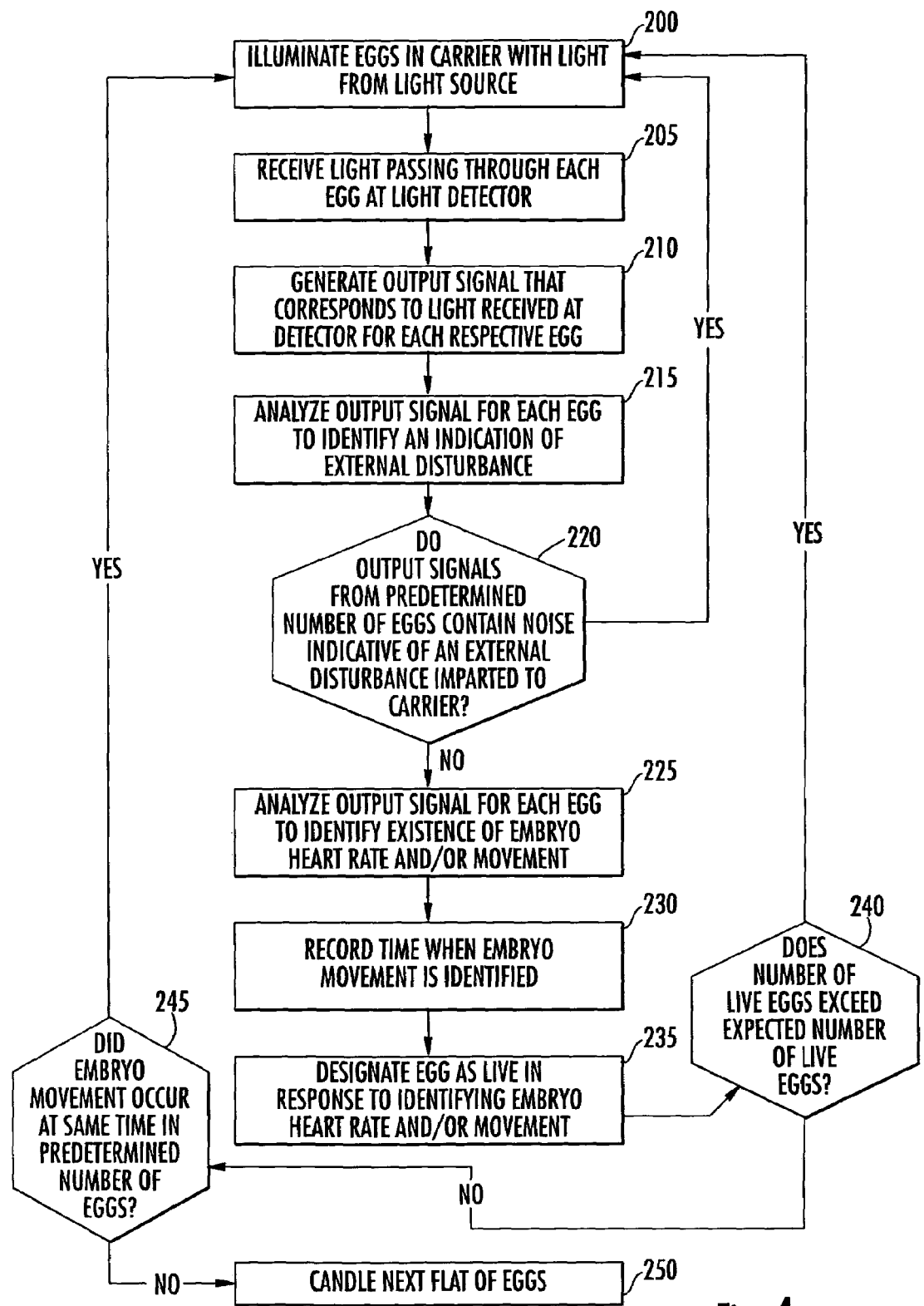

Referring now to FIG. 4, methods of identifying live and non-live eggs, according to embodiments of the present invention, are illustrated. Initially, each of a plurality of presumably embryonated eggs in a carrier (e.g., an egg flat) are candled to detect embryo motion and/or embryo heart rate. Candling is performed by illuminating the eggs in a flat with light from a light source (Block 200) and receiving light passing through each egg at a detector (Block 205). An output signal that corresponds to light received at a detector is generated for each respective egg (Block 210). An exemplary candling method for measuring embryo motion and/or heart rate for each egg in a group of eggs uses an optical system that illuminates each egg and measures the light coming from each egg as described in U.S. Pat. No. 6,860,225 to Hebrank. However, various other methods and apparatus for measuring embryo motion and/or heart rate can be utilized, without limitation.

The output signal for each egg is analyzed (e.g., by processor 40 of FIG. 2) to identify an indication (e.g., noise and/or waveforms, etc.) of an external disturbance imparted to the flat (e.g., vibrations, the flat being bumped, etc.) (Block 215). A determination is made whether output signals from a predetermined number of eggs contain an indication of an external disturbance (Block 220). If the answer is yes, the eggs in the flat are recandled (Blocks 200-215) because it is likely that the eggs in the flat have experienced an external disturbance of some type. If the answer is no, the output signal for each egg is analyzed (e.g., by processor 40 of FIG. 2) to identify the existence of an embryo heart rate and/or embryo movement (Block 225). If embryo movement was detected, the time when embryo movement was detected is recorded (Block 230). Each egg is then designated as live or non-live in response to identifying, or failing to identify, embryo heart rate and/or embryo movement (Block 235), and the live/non-live data is stored.

The number of eggs in the flat designated as live is compared with an expected number (Block 240) and, if the number exceeds the expected number, the eggs in the flat are recandled (Blocks 200-215) because it is likely that the egg flat has experienced an external disturbance of some type which falsely indicates more live eggs. If the number is less than the expected number, a determination is made whether embryo movement occurred at the same time in a predetermined number of eggs (Block 245). If the answer is yes, the, eggs in the flat are recandled (Blocks 200-215) because it is likely that the egg flat has experienced an external disturbance of some type which falsely indicates more live eggs. If the answer is no, the current flat of eggs is moved along for further processing and a new flat is moved in for candling (Block 250) and operations of Blocks 200-245 are repeated as described above.

In the embodiment illustrated by FIG. 4, if re-candling is required, the re-candling interval will typically be quicker than the initial candling interval since the eggs are already in position for candling and the candler filter circuits are already stabilized from the transition of the illuminating lamps being turned on.

According to one embodiment of the present invention, a motion/heart rate candling system dedicates a microprocessor to each or several eggs and all of the detection microprocessors communicate with a central processor that coordinates the candling process and that also sends the live/dead information for each egg to apparatus for picking the eggs from the flat (e.g., egg removal station 50, FIG. 2) and/or marking the eggs. This central processor is configured to query each of the microprocessors for specific information, such as the time of motion detection, time of all light variations greater than a preset value, etc. In FIG. 2, processor 40 is intended to inclusively represent a central processor and any microprocessors in communication therewith.

According to a second embodiment of the present invention, a motion/heart rate candling system dedicates an analog filter system to each egg and the signal from each analog filter system is digitized, stored and analyzed in one or more central processors, thus utilizing the processing power of a single central system to extract motion and heartbeat information. Having digitized waveforms for each egg available for collective analysis simplifies detection of environmental vibration that affects multiple eggs by correlating similarities in time or character of the recorded signals. The central processor also coordinates the candling process and sends the live/dead information for each egg to apparatus for picking the eggs from the flat (e.g., egg removal station 50, FIG. 2) and/or marking the eggs. In FIG. 2, processor 40 is intended to inclusively represent a central processor.

Where heart rate detection is being determined for diagnostic purposes, as described below, communication and correlation of motion artifacts can lessen the possibility that heart rate calculations would be skewed from motion artifacts. In flu vaccine production where eggs are kept in cooler incubators to aid virus growth, the cooler embryos will likely have less motion. As such, external vibrations affecting multiple eggs should be more easily detectable.

In situations where maximally quick detection of a live egg is achieved by the sensing of embryo motion or just one or two heart beats, eliminating false heartbeats from vibration can be critical to the reduction of false lives.

Figure 5:
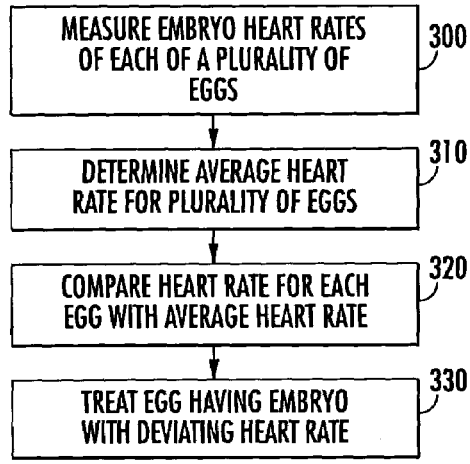
FIGS. 5-8 are flowcharts of operations for determining the condition of egg embryos, according to embodiments of the present invention.

Referring now to FIG. 5, methods of using embryo heart rate as a diagnostic tool, in accordance with embodiments of the present invention, are illustrated. The embryo heart rate of each of a plurality of presumably embryonated eggs in a carrier (e.g., a flat of eggs) is initially measured (Block 300). An exemplary method of measuring embryo heart rate for each egg in a group of eggs uses an optical system that illuminates each egg and measures the light coming from each egg as described in U.S. Pat. No. 6,860,225 to Hebrank. However, various other methods and apparatus for measuring embryo heart rate can be utilized, without limitation.

An average heart rate is then determined for the plurality of eggs (Block 310). The respective heart rate for each egg is then compared with the average heart rate to identify eggs having embryos with heart rates that deviate from the average heart rate (Block 320). A deviating heart rate (i.e., a higher heart rate than average or a lower heart rate than average) may indicate a negative health condition of an embryo, for example. In response to identifying an egg having an embryo with a deviating heart rate (and thus possibly a negative health condition, or some other condition), a treatment of the egg may be performed that is designed to improve the negative (or other type of) health condition of the embryo (Block 330). Exemplary treatments includes, but are not limited to, cracking the egg air cell to aid pipping, placing the egg in an oxygen-enhanced environment, placing the egg in a warmer environment, and injecting material into the egg. Exemplary material that may be injected into an egg to improve the health condition of the egg includes, but is not limited to, vaccines, medications, nutrients, and hormones. For example, thyroid releasing hormone (TRH) may be injected into a egg to increase the likelihood of an embryo hatching.

Figure 6:
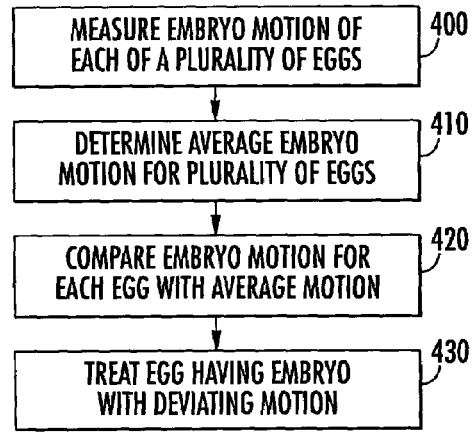

Referring now to FIG. 6, methods of using embryo motion as a diagnostic tool, in accordance with embodiments of the present invention, are illustrated. The motion of an embryo within each of a plurality of presumably embryonated eggs in a carrier (e.g., a flat of eggs) is initially measured (Block 400). An exemplary method of measuring embryo motion for each egg in a group of eggs uses an optical system that illuminates each egg and measures the light coming from each egg as described in U.S. Pat. No. 6,860,225 to Hebrank. However, various other methods and apparatus for measuring embryo motion can be utilized, without limitation.

An average motion is then determined for the plurality of eggs (Block 410). Motion for each egg may be measured as the maximum peak to peak value during the few seconds of monitor, or may be the spectral energy in frequencies from about 0.2 Hz to about 2 Hz. The respective embryo motion for each egg is compared with the average embryo motion to identify eggs having embryos with motion that deviates from the average motion (Block 420). A deviating amount of motion (i.e., less motion than average or higher motion than average) may indicate a negative health condition (or other type of condition) of an embryo. In response to identifying an egg having an embryo with deviating motion (and thus possibly a negative health condition, or other type of condition), a treatment of the egg may be performed that is designed to improve the negative health condition (or other type of condition) of the embryo (Block 430). As described above, exemplary treatments include, but are not limited to, cracking the egg air cell to aid pipping, placing the egg in an oxygen-enhanced environment, placing the egg in a warmer environment, and injecting material into the egg. Exemplary material that may be injected into an egg to improve the health condition of the egg includes, but is not limited to, vaccines, medications, nutrients, and hormones. For example, TRH may be injected into a egg to increase the likelihood of an embryo hatching.

Various methods of measuring embryo heart rates and movement may be used in accordance with embodiments of the present invention. For example, each egg may be illuminated with light from a light source (e.g., either or both visible and infrared wavelengths). Light leaving each egg is then received by a photodetector positioned adjacent each egg. Each photodetector generates an output signal that corresponds to the intensity of light leaving a respective egg. The output signal is processed to determine the embryo heart rate of each respective egg. For example, an output signal may be processed to determine the existence of cyclical variations in light intensity that correspond to an embryo heart rate. In addition, an output signal may be processed to determine the existence of non-cyclical variations in light intensity that correspond to embryo movement within an egg.

Figure 7:
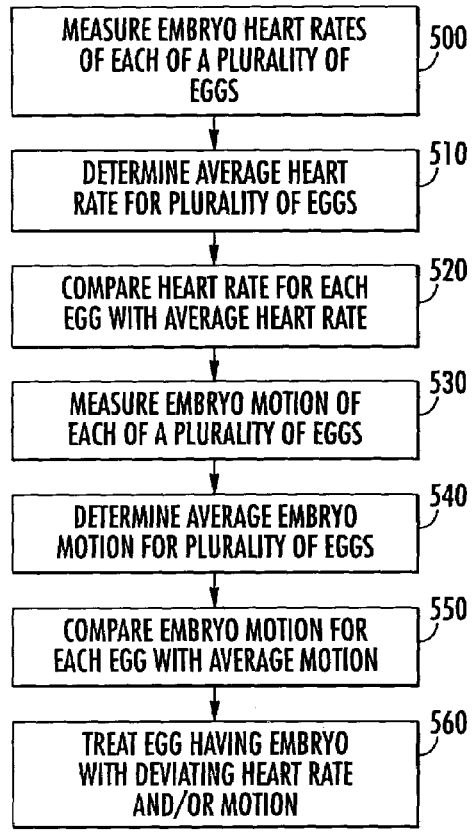

Referring now to FIG. 7, methods of using embryo heart rate and motion as a diagnostic tool, in accordance with embodiments of the present invention, are illustrated. The embryo heart rates of each of a plurality of presumably embryonated eggs in a carrier (e.g., a flat of eggs) are initially measured (Block 500). An average embryo heart rate is then determined for the plurality of eggs (Block 510). The respective embryo heart rate for each egg is compared with the average embryo heart rate to identify eggs having embryos with heart rates that deviate from the average heart rate (Block 520). A deviating heart rate (i.e., a higher heart rate than average or a lower heart rate than average) may indicate a negative health condition (or other type of condition) of an embryo. The motion of an embryo within each of the plurality of eggs is also measured (Block 530), and an average motion is calculated for the plurality of eggs (Block 540). The respective embryo motion for each egg is compared with the average embryo motion to identify eggs having embryos with motion that deviates from the average motion (Block 550). A deviating amount of motion (i.e., less motion than average or higher motion than average) may indicate a negative health condition (or other type of condition) of an embryo.

In response to identifying an egg having an embryo with a negative health condition (or other type of condition) by either heart rate detection or motion detection (or a combination of both), a treatment of the egg is performed that is designed to improve the negative health condition (or other type of condition) of the embryo (Block 560). As described above, exemplary treatments include, but are not limited to, cracking the egg air cell to aid pipping, placing the egg in an oxygen-enhanced environment, placing the egg in a warmer environment, and injecting material into the egg. Exemplary material that may be injected into an egg to improve the health condition of the egg includes, but is not limited to, vaccines, medications, nutrients, and hormones. For example, TRH may be injected into a egg to increase the likelihood of an embryo hatching.

Figure 8:
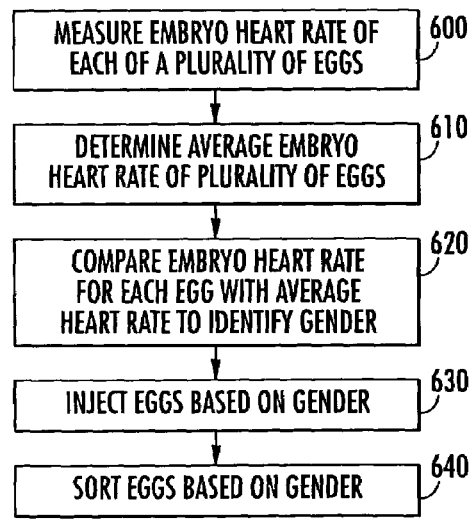

Referring now to FIG. 8, methods of using embryo heart rate as an indicator of gender, in accordance with embodiments of the present invention, are illustrated. The embryo heart rates of each of a plurality of presumably embryonated eggs in a carrier (e.g., a flat of eggs) are initially measured (Block 600). An average embryo heart rate is then determined for the plurality of eggs (Block 610). The respective embryo heart rate for each egg is compared with the average embryo heart rate to identify the gender of the embryo in each egg (Block 620). A vaccine or other treatment substance may be injected into the eggs (or material may be removed from the eggs) according to gender (Block 630). In addition, eggs may be sorted according to embryo gender (Block 640). Sorting based on gender may occur prior to or after injecting a substance into the eggs.

Sorting may include designating an egg as male, female, or gender uncertain. Eggs designated as gender uncertain may be subjected to further operations, such as hand candling, for example, in order to determine gender with more certainty. See, for example, U.S. Pat. No. 6,750,954.

In addition to use with gender sorting and health diagnostics, as described herein, embodiments of the present invention can facilitate flu vaccine production. For example, the identification of embryonic heart rates that deviate from the average heart rate of a plurality of eggs used in the production of flu vaccine can indicate contaminated eggs and/or improperly inoculated eggs (e.g., eggs that did not have a seed virus placed properly within the allantois, etc.).

According to other embodiments of the present invention, the correlation of embryo heart rate with one or more other egg characteristics may be utilized to accurately detect health conditions, gender and other aspects of eggs. For example, heart rate may be correlated with egg temperature to detect a condition of an embryo. In addition, heart rate may be correlated with egg shell size and/or weight to detect a condition of an embryo.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of identifying live eggs, comprising:
   a) illuminating eggs in a carrier with light from a light source;
   b) receiving light passing through each egg at a light detector;
   c) generating an output signal that corresponds to light received at a light detector for each respective egg; and
   d) analyzing the output signals for the eggs to identify an indication of an external disturbance imparted to the carrier.

2. The method of claim 1, wherein an indication of an external disturbance comprises noise in an output signal.

3. The method of claim 1, wherein an indication of an external disturbance comprises one or more waveforms in an output signal.

4. The method of claim 1, further comprising repeating steps a) through d) in response to determining that output signals from a predetermined number of eggs contain an indication of an external disturbance imparted to the carrier.

5. The method of claim 1, further comprising:
   e) analyzing the output signal for each egg to identify the existence of an embryo heart rate and/or embryo movement; and
   f) designating an egg as a live egg in response to identifying embryo heart rate and/or embryo movement.

6. The method of claim 5, further comprising:
   comparing the number of eggs designated as live with an expected number; and
   repeating steps a) through f) in response to determining that the number of eggs designated as live exceeds the expected number.

7. The method of claim 5, further comprising:
   recording the time at which embryo movement is identified; and repeating steps a) through f) in response to determining that embryo movement occurred at about the same time in a predetermined number of eggs.

8. The method of claim 1, further comprising:
recording the time at which a particular output signal occurred for each egg; and
repeating steps a) through d) in response to determining that a particular output signal occurred at about the same time in a predetermined number of eggs.

9. The method of claim 8, wherein a particular output signal comprises a waveform maximum or a waveform zero crossing.

10. A method of identifying live eggs, comprising:
a) illuminating eggs in a carrier with light from a light source;
b) receiving light passing through each egg at a light detector;
c) generating an output signal that corresponds to light received at a light detector for each respective egg;
d) analyzing the output signals for the eggs to identify an indication of an external disturbance imparted to the carrier;
e) analyzing the output signal for each egg to identify the existence of an embryo heart rate;
f) designating an egg as a live egg in response to identifying embryo heart rate; and
g) comparing the number of eggs designated as live with an expected number and repeating steps a) through f) in response to determining that the number of eggs designated as live exceeds the expected number.

11. The method of claim 10, wherein an indication of an external disturbance comprises noise in an output signal.

12. The method of claim 10, wherein an indication of an external disturbance comprises one or more waveforms in an output signal.

13. The method of claim 10, further comprising:
recording the time at which a particular output signal occurred for each egg; and
repeating steps a) through d) in response to determining that a particular output signal occurred at about the same time in a predetermined number of eggs.

14. The method of claim 13, wherein a particular output signal comprises a waveform maximum or a waveform zero crossing.

15. A method of identifying live eggs, comprising:
a) illuminating eggs in a carrier with light from a light source;
b) receiving light passing through each egg at a light detector;
c) generating an output signal that corresponds to light received at a light detector for each respective egg; and
d) analyzing the output signals for the eggs to identify an indication of an external disturbance imparted to the carrier.
e) analyzing the output signal for each egg to identify the existence of embryo movement;
f) designating an egg as a live egg in response to identifying embryo movement;
g) recording the time at which embryo movement is identified; and
h) repeating steps a) through f) in response to determining that embryo movement occurred at about the same time in a predetermined number of eggs.

16. The method of claim 15, wherein an indication of an external disturbance comprises noise in an output signal.

17. The method of claim 15, wherein an indication of an external disturbance comprises one or more waveforms in an output signal.

18. The method of claim 15, further comprising repeating steps a) through d) in response to determining that output signals from a predetermined number of eggs contain an indication of an external disturbance imparted to the carrier.

19. A candling apparatus that identifies live eggs among a plurality of eggs within a carrier, comprising:
a light source that illuminates one or more eggs within the carrier with light;
a detector that receives light passing through one or more eggs from the light source and that generates an output signal corresponding to the received light; and
a processor configured to analyze the output signal for each egg for the existence of embryo heart rate and/or embryo movement, wherein the processor is configured to designate an egg as a live egg in response to identifying embryo heart rate and/or embryo movement, and wherein the processor is configured to analyze the output signal for each egg to identify an indication of an external disturbance imparted to the carrier.

20. The candling apparatus of claim 19, wherein an indication of an external disturbance comprises noise in an output signal.

21. The candling apparatus of claim 19, wherein an indication of an external disturbance comprises one or more waveforms in an output signal.

22. The candling apparatus of claim 19, wherein the processor is configured to require that the plurality of eggs be recandled in response to determining that output signals from a predetermined number of eggs contain an indication of an external disturbance.

23. The candling apparatus of claim 19, wherein the processor is configured to compare the number of eggs designated as live with an expected number, and wherein the processor is configured to require that the plurality of eggs be recandled in response to determining that the number of eggs designated as live exceeds an expected number.

24. The candling apparatus of claim 19, wherein the processor is configured to record the time at which embryo motion is identified for each egg, and wherein the processor is configured to require that the plurality of eggs be recandled in response to determining that embryo movement occurred at about the same time in a predetermined number of eggs.

25. A candling apparatus that identifies live eggs among a plurality of eggs within a carrier, comprising:
a light source that illuminates one or more eggs within the carrier with light;
a detector that receives light passing through one or more eggs from the light source and that generates an output signal corresponding to the received light; and
a processor configured to:
analyze the output signal for each egg to identify the existence of an embryo heart rate;
designate an egg as a live egg in response to identifying a heart rate; and
compare the number of eggs designated as live with an expected number of live eggs and require that the plurality of eggs be recandled in response to determining that the number of eggs designated as live exceeds the expected number of live eggs.

26. A candling apparatus that identifies live eggs among a plurality of eggs within a carrier, comprising:

a light source that illuminates one or more eggs within the carrier with light;

a detector that receives light passing through one or more eggs from the light source and that generates an output signal corresponding to the received light; and a processor configured to:

analyze the output signal for each egg to identify the existence of embryo movement;

designate an egg as a live egg in response to identifying embryo movement;

record the time at which embryo movement is identified; and require that the plurality of eggs be recandled in response to determining that embryo movement occurred at about the same time in a predetermined number of eggs.

27. A method of diagnosing embryo health of a plurality of eggs, comprising:

measuring heart rates of each of a plurality of eggs;

determining an average heart rate for the plurality of eggs;

comparing the respective heart rate for each egg with the average heart rate to identify eggs having embryos with heart rates that deviate from the average heart rate; and performing one or more of the following functions in response to identifying an egg having a deviating heart rate: cracking the egg air cell to aid pipping, placing the egg in an oxygen-enhanced environment, placing the egg in a warmer environment, and injecting material into the egg.

28. The method of claim 27, further comprising:

measuring embryo motion of each of the plurality of eggs;

determining average embryo motion for the plurality of eggs; and comparing the respective embryo motion for each egg with the average embryo motion to identify eggs having embryo motion that deviates from the average embryo motion.

29. The method of claim 27, wherein injecting material into the egg comprises injecting material selected from the group consisting of: vaccines, medications, nutrients, and hormones.

30. The method of claim 27, wherein injecting material into the egg comprises injecting TRH into the egg.

31. A method of identifying the gender of a plurality of eggs, comprising:

measuring heart rates of each of a plurality of eggs;

determining an average heart rate for the plurality of eggs; and comparing the respective heart rate for each egg with the average heart rate to identify a gender of each egg.

32. The method of claim 31, further comprising selectively injecting a substance into the eggs according to gender.

33. The method of claim 31, further comprising selectively removing material from the eggs according to gender.

34. The method of claim 32, further comprising sorting the eggs according to gender prior to injecting a substance into the eggs.

35. The method of claim 33, further comprising sorting the eggs according to gender prior to removing material from the eggs.

36. The method of claim 32, further comprising sorting the eggs according to gender after injecting a substance into the eggs.

37. The method of claim 33, further comprising sorting the eggs according to gender after removing material from the eggs.

* * * * *